(12) United States Patent
Vaz Viegas et al.

(10) Patent No.: US 9,556,577 B2
(45) Date of Patent: Jan. 31, 2017

(54) SUSTAINABLE FILTERING DEVICE FOR COLLECTING FLOATING DEBRIS

(71) Applicant: IHC HOLLAND IE B.V., Molendijk (NL)

(72) Inventors: Pedro Vaz Viegas, Setubal (PT); Maria Bernardete Goncalves Castro, Dordrecht (NL); Edwin Albert Munts, Zwijndrecht (NL)

(73) Assignee: IHC HOLLAND IE B.V., Sliedrecht (NL)

( * ) Notice: Subject to any disclaimer, the term of this patent is extended or adjusted under 35 U.S.C. 154(b) by 213 days.

(21) Appl. No.: 14/378,017

(22) PCT Filed: Feb. 11, 2013

(86) PCT No.: PCT/NL2013/050080
§ 371 (c)(1),
(2) Date: Aug. 11, 2014

(87) PCT Pub. No.: WO2013/119123
PCT Pub. Date: Aug. 15, 2013

(65) Prior Publication Data
US 2015/0034565 A1    Feb. 5, 2015

(30) Foreign Application Priority Data

Feb. 10, 2012 (NL) .................................... 2008274

(51) Int. Cl.
*E02B 15/10* (2006.01)
*E02B 15/04* (2006.01)
(Continued)

(52) U.S. Cl.
CPC .............. *E02B 15/10* (2013.01); *B63B 35/32* (2013.01); *C02F 1/001* (2013.01); *E02B 15/00* (2013.01);
(Continued)

(58) Field of Classification Search
CPC ........ E02B 15/00; E02B 15/04; E02B 15/046; E02B 15/047; E02B 15/048; E02B 15/10; B63B 35/32; B63B 2001/123; B63B 2035/007
(Continued)

(56) References Cited

U.S. PATENT DOCUMENTS 3,268,081 A * 8/1966 Menkee ................ E02B 15/046
210/242.1
3,653,510 A * 4/1972 Fitzgerald ............. E02B 15/048
210/776
(Continued)

FOREIGN PATENT DOCUMENTS

CN    201 228 077 Y    2/1979
CN    100 368 257 C    2/2008
(Continued)

OTHER PUBLICATIONS

International Search Report, dated Apr. 25, 2013, from corresponding PCT application.

*Primary Examiner* — Christopher Upton
(74) *Attorney, Agent, or Firm* — NLO N.V.; Catherine A. Shultz; Minerva Rivero

(57) ABSTRACT

An assembly for being dragged by a vessel, wherein the assembly includes a filtering system and a fluidum guiding system, wherein the filtering system is suitable for filtering large volumes of fluidum, and wherein the fluidum guiding system defines a channel configured such that at least in a channel portion the current velocity of the fluidum guided through that channel portion is reduced downstream, and wherein the fluidum guiding system and the filtering system are mutually arranged such that current velocity of fluidum filtered in the filtering system is reduced for decreasing drag.

19 Claims, 2 Drawing Sheets

(51) Int. Cl.
*B63B 35/32* (2006.01)
*E02B 15/00* (2006.01)
*G01N 1/02* (2006.01)
*G01N 1/20* (2006.01)
*C02F 1/00* (2006.01)
*C02F 103/00* (2006.01)
*G01N 1/10* (2006.01)
*B63B 1/12* (2006.01)
*B63B 35/00* (2006.01)
*C02F 103/08* (2006.01)

(52) U.S. Cl.
CPC ............... *E02B 15/046* (2013.01); *G01N 1/02* (2013.01); *G01N 1/2035* (2013.01); *B63B 2001/123* (2013.01); *B63B 2035/007* (2013.01); *C02F 2103/007* (2013.01); *C02F 2103/08* (2013.01); *C02F 2201/002* (2013.01); *C02F 2201/008* (2013.01); *G01N 2001/028* (2013.01); *G01N 2001/1006* (2013.01)

(58) Field of Classification Search
USPC .............. 210/170.05, 170.09, 170.1, 170.11, 210/242.1, 747.6, 776
See application file for complete search history.

(56) References Cited

U.S. PATENT DOCUMENTS

| | | | | |
|---|---|---|---|---|
| 3,669,275 A | * | 6/1972 | Downs | ............... E02B 15/10 210/242.4 |
| 3,831,756 A | | 8/1974 | Bhuta et al. | |
| 4,362,631 A | * | 12/1982 | Bocard | ................ E02B 15/048 210/776 |
| 5,019,277 A | * | 5/1991 | Andelin | ................ E02B 15/106 210/776 |
| 2013/0082007 A1 | * | 4/2013 | Kennedy | ................ E02B 15/06 210/747.6 |
| 2013/0146519 A1 | * | 6/2013 | Heimtun | ................ E02B 15/048 210/242.1 |

FOREIGN PATENT DOCUMENTS

| | | |
|---|---|---|
| CN | 101 451 353 A | 6/2009 |
| CN | 201 895 760 U | 7/2011 |
| EP | 1 439 119 B1 | 3/2011 |
| FR | 2 061 978 A5 | 6/1971 |
| GB | 369715 A | 3/1932 |
| GB | 1 322 121 A | 7/1973 |
| JP | 54 018895 U | 2/1979 |
| JP | 54 107088 A | 8/1979 |
| JP | 58 216784 A | 12/1983 |
| JP | 60 073910 A | 4/1985 |
| JP | 6 346502 A | 12/1994 |
| NL | 1 003 662 C1 | 9/1996 |
| WO | 92/16693 A1 | 1/1992 |
| WO | 97/01680 A1 | 1/1997 |

* cited by examiner

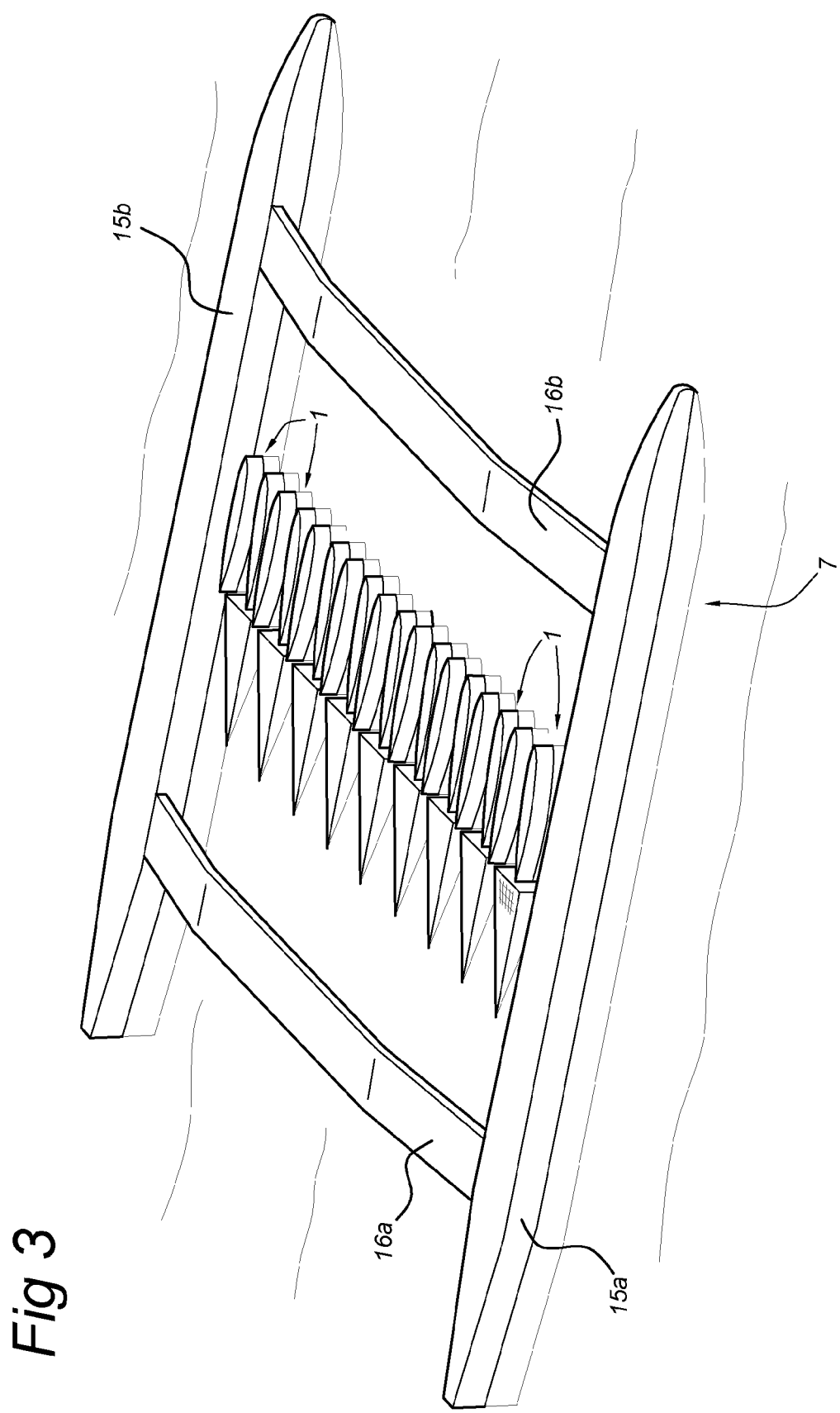

SUSTAINABLE FILTERING DEVICE FOR COLLECTING FLOATING DEBRIS

BACKGROUND

The present invention relates to an assembly of a filtering system and a fluidum guiding system, wherein the filtering system is suitable for filtering large volumes of fluidum.

The present invention further relates to a vessel comprising an assembly according to the invention.

The present invention further relates to the use of an assembly according to the invention for collecting particles from sea in particular pollution, like plastic particles.

Such an assembly is known from WO9701680A1 which discloses a floating debris collection device comprising flotation members which define a channel into which water and floating debris can flow at a first end towards a second end, first and second closure means for the channel adjacent said first and second ends respectively, the first and second closure means each being adapted to restrict floating debris but not water in the channel from flowing out of the channel; the first closure means being movable between an open position in which water and floating debris can flow into the channel and a closed position in which floating debris but not water in the channel is substantially restricted from flowing out of the channel; and means sensitive to the direction of water flow with respect to the channel for moving the first closure means between said open and closed positions. However the assembly of WO9701680A1 is not particularly suitable for being dragged through the water.

It is also known, from e.g. GB 369,715 A, to use instruments for determining the nature and quantity of planktonic organisms present in sea water. These instrument typically consist of an open-ended cylinder which is configured to be dragged at relatively high speed. In addition these scientific instruments are intended to filter low volumes of sea water and the residu having quantities as required for research purposes.

Filter systems described in the prior art, such as in FR2061978A5, have a relatively high drag, as such filter systems have a configuration in which the velocity of the fluid is increased towards the filtering system such that current velocity of fluidum filtered in the filtering system is increased.

SUMMARY OF THE INVENTION

The invention aims to provide an assembly of a filtering system and a fluidum guiding system which is more efficient in use. Efficient is to say, able to collect more residue per unit power consumption.

Another object of the invention is to improve an alternative assembly of a filtering system and a fluidum guiding system.

Yet another object of the invention is to provide an assembly of a filtering system and a fluidum guiding system wherein a problem of a known assembly is at least partly solved.

According to a first aspect of the invention this is realized with an assembly for being dragged by a vessel, wherein the assembly comprises a filtering system and a fluidum guiding system, wherein the filtering system is suitable for filtering large volumes of fluidum, and wherein the fluidum guiding system defines a channel configured such that at least in a channel portion the current velocity of the fluidum guided through that channel portion is reduced downstream, and wherein the fluidum guiding system and the filtering system are mutually arranged such that current velocity of fluidum filtered in the filtering system is reduced for decreasing drag. The fluidum guiding system of the assembly enables that the pressure losses of the filtering process in the filtering system are reduced because the velocity of fluidum actually filtered is reduced, which results in a lower drag of the assembly. This assembly improves the economical and environmental feasibility of filtering large amounts of fluids because the energy required for filtering is importantly reduced. This assembly is particularly useful in connection with filtering plastic debris, specifically micro-debris, out of the sea or any other body of water. Thus, the drag reduction leads to lower energy consumption, which enables the economical and environmental friendly removal of plastic debris from water bodies. The assembly is particularly useful for the economical and environmental friendly removal of plastic micro-debris from water bodies.

The filtering system of the assembly is suitable for filtering large volumes of fluidum. Here, large volumes has to be explained such that, in use, the assembly has significant positive effect to the environment wherein the assembly operates. The invention allows large volumes of fluidum to be filtered with a significant drag reduction, and thereby with much lower energy requirement. This provides a big advantage with respect to the prior art, in which the fluidum is accelerated through the filtering unit, with the consequence of a large energy requirement for either filtering or positioning. The reduction of the amount of energy needed allows to power the filtering system with a renewable energy source.

With respect to the filtering system different types of filters can be used like for example a plankton net, baleen filters, filtering rolls, a hydrocyclone and a membrane or combinations thereof. In addition, it is conceivable to combine multiple filtering systems in series to filter a wide size range of particles. Also, a custom build net like a net with various mesh openings may be used.

The assembly is suitable for being dragged by a vessel. It will be clear however that the invention may be useful to pipe circuits as well, in which pipe circuit the assembly then is arranged in the flow through the pipe circuit for filtering debris out of the flow.

In an embodiment of the invention, the filtering system comprises an inlet for allowing fluidum to be filtered to enter the filtering system, and wherein the fluidum guiding system is arranged for reducing current velocity of fluidum to be filtered downstream towards the inlet. In other words current velocity of fluidum, which in use enters the inlet, is reduced.

In an embodiment of the invention, the cross-sectional area of the channel portion increases downstream for reducing speed of the fluidum to be filtered. This is different from the prior art, for instance FR2061978A5, wherein the speed of the fluidum is increased, thus drag is increased.

In an embodiment of the invention, the fluidum guiding system at least partly encloses the filter system for reducing drag. This even more reduces drag of the assembly because not only speed of the fluidum to be filtered is reduced, but also turbulence caused by the assembly is reduced.

In an embodiment of the invention, the fluidum guiding system encloses substantially the entire filter system for reducing drag.

In an embodiment of the invention, the filtering system comprises a netting with a mesh configured such that particles of contamination, like e.g. particles of plastic, are filtered out of the fluidum. The mesh is such that the assembly will have to be dragged at a relatively low speed of about 1 m/s in order to even more reduce drag such that an economical and environmental friendly removal of plastic debris, in particular micro-debris, from water bodies is obtained. The mesh is typically such that particles in order of several cm's, in case of micro-debris several mm's, are filtered from the seawater.

In an embodiment of the invention, the filtering system comprises an outlet for allowing filtered out particles to leave the filtering system. This enables a common processing downstream in case of a plurality of assemblies in parallel.

In an embodiment of the invention, the fluidum guiding system comprises opposing side members and a bottom member which are joined together for defining the channel. This enables a free sight from above the channel which is beneficial in case of malfunction of maintenance.

In an embodiment of the invention, at least one side member comprises a curved portion. This even more reduces drag of the assembly and/or turbulence caused by the assembly. It will be clear that adjustments in the geometry of the side members and bottom member can be made to provide the lowest drag possible in each situation.

In an embodiment of the invention, the channel is open at its upper side.

According to a further aspect of the invention this is realized with a vessel comprising an assembly according to the invention, wherein the vessel, in use, drags the assembly and the vessel is configured for operation at low travelling speed, like lower than 2 m/s, for example 1 m/s. In this connection low travelling speed is a speed that on the one hand matches with the the mesh of the netting of the filtering system and on the other side ensures an environmental friendly operation of the vessel.

In an embodiment of the invention, the vessel comprises an adjusting device which couples the assembly and the vessel for adjusting the height position of the assembly relative to the water surface.

In an embodiment of the invention, the vessel comprises a plurality of assemblies.

In an embodiment of the vessel, the assemblies are arranged side by side in a row.

In an embodiment of the vessel, respective outlets of at least two filtering devices are coupled with a common conduit for collecting residue.

In an embodiment of the invention, the vessel is driven using solar and/or wind power, preferably using only solar and/or wind power. This even more ensures an environmental friendly operation of the vessel and enables a true zero polution operation of the vessel.

In an embodiment of the invention, the vessel comprises control means such that the vessel is an autonomous unmanned vessel.

The invention also relates to a pipe circuit for transporting a flow, the pipe circuit comprising an assembly according to the invention, wherein the assembly is arranged in the flow for filtering debris out of the flow.

According to an even further aspect of the invention this is realized with an use of an assembly according to the invention for collecting particles from water bodies, like the sea, in particular pollution, like plastic particles.

In an embodiment of the use, the vessel travels at low speed, like lower than 2 m/s, for example 1 m/s.

The invention further relates to a device comprising one or more of the characterising features described in the description and/or shown in the attached drawings.

The invention further relates to a method comprising one or more of the characterising features described in the description and/or shown in the attached drawings.

The various aspects discussed in this patent can be combined in order to provide additional advantages.

DESCRIPTION OF THE DRAWINGS

The invention will be further elucidated referring to embodiments shown in the drawing wherein shown in:

and FIG. 3 a vessel comprising a plurality of assemblies of FIG. 1.

DETAILED DESCRIPTION OF EMBODIMENTS

Figure 1:
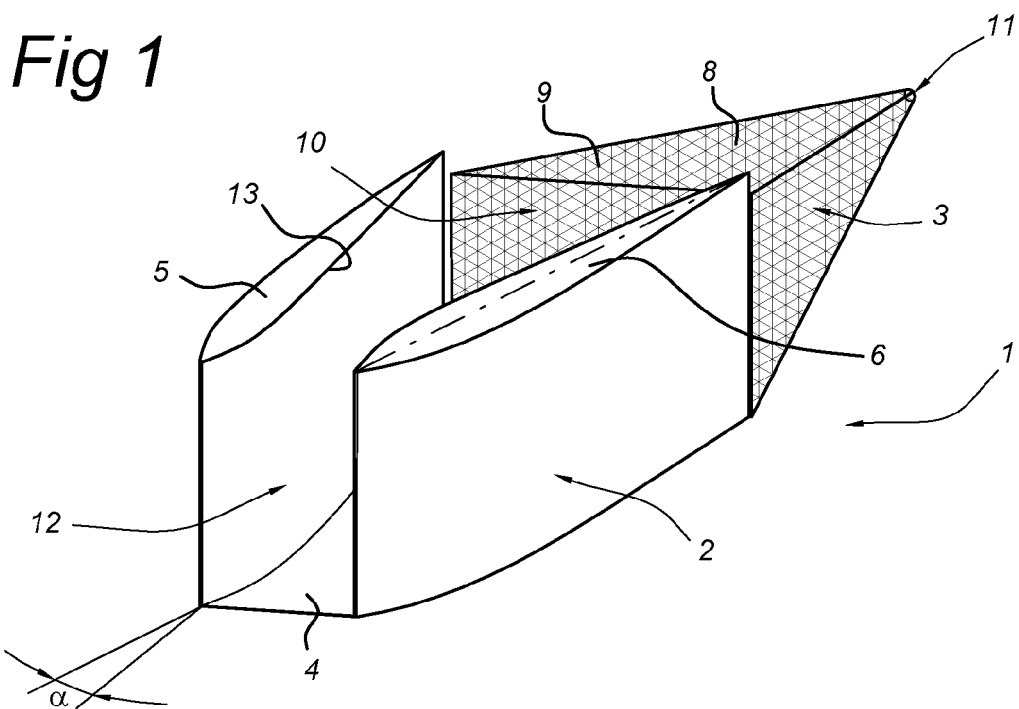
FIG. 1 in perspective view an assembly according to the invention.
Figure 2A:
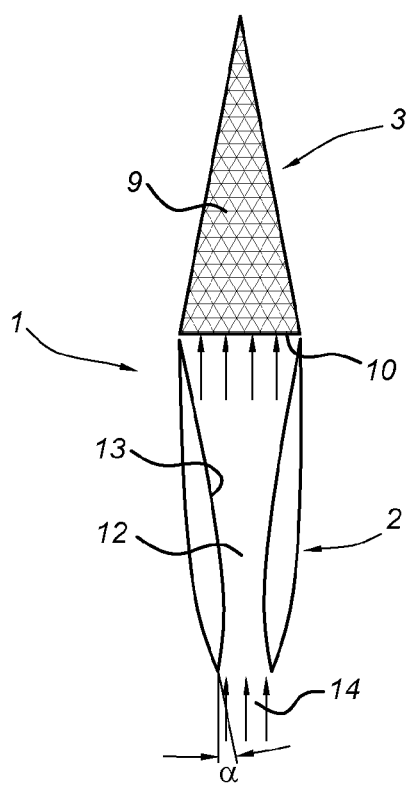
FIG. 2a a top view of the assembly according to FIG. 1.
Figure 2B:
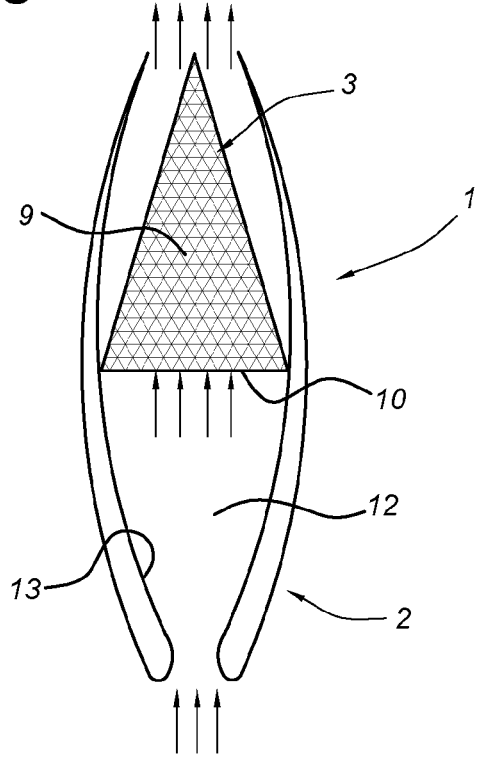
FIG. 2b a top view of a further embodiment of the assembly according to the invention.

In the figures FIG. 1 discloses in perspective view an assembly 1. FIG. 2a shows a top view of the assembly 1 according to FIG. 1. FIG. 2b depicts a top view of a further embodiment of the assembly 1. FIG. 3 shows a vessel 7 comprising a plurality of assemblies 1 of FIG. 1. The invention will be described referring to all figures.

The Assembly 1 is suitable for being dragged by a vessel 7. When the assembly 1 is dragged by a vessel 7, a flow resistance will occur which needs to be overcome by the vessel 7. This flow resistance is referred to as drag.

The assembly 1 comprises a filtering system 3. The filtering system 3 is suitable for filtering large volumes of fluidum 14, in this case (sea) water. The filtering system 3 comprises an inlet 10 for allowing fluidum to be filtered to enter the filtering system 3. Usually the inlet 10 is framed (not shown) for maintaining the shape of inlet 10. Here, the filtering system 3 comprises a netting 8. The netting is provided with a mesh 9 configured such that particles of contamination, like e.g. particles of plastic, are filtered out of the fluidum. The filtering system 3 comprises an outlet 11 for allowing filtered out particles to leave the filtering system 3.

The assembly 1 comprises a fluidum guiding system 2. The fluidum guiding system 2 defines a channel 12 configured such that at least in a channel portion the current velocity of the fluidum 14 guided through that channel portion is reduced downstream. Here, the cross-sectional area of the channel portion increases downstream for reducing speed of the fluidum 14 to be filtered. The fluidum guiding system 2 comprises opposing side members 5, 6 and a bottom member 4 which are joined together for defining the channel 12. Here, both side members 5, 6 comprises a curved portion 13. The geometry of the side members 5, 6 reduces the velocity of the fluidum at the inlet 10 of the filtering system 3. The curved portion 13, which constitutes a hydrodynamic shape, guarantees a smooth flow, resulting in a low drag assembly 1.

Here, the channel 12 is open at its upper side. It is conceivable however to employ a circumferential conduit which defines the channel 12.

The fluidum guiding system 2 and the filtering system 3 are mutually arranged such that current velocity of fluidum 14 filtered in the filtering system 3 is reduced for decreasing drag. Here, the fluidum guiding system 2 is arranged for reducing current velocity of fluidum to be filtered downstream towards the inlet 10.

In FIG. 2a, the fluidum guiding system 2 is placed at the inlet 10 of the filtering system 3 to limit the unwanted inflow of fluidum from higher pressure zones outside the filtering area of the assembly.

In FIG. 2b the fluidum guiding system 2 encloses substantially the entire filtering system for reducing drag.

The vessel 7 of FIG. 3 is a catamaran type of vessel 7 with two opposing floating bodies 15a, 15b joined by two tranverse connection profiles 16a, 16b. The vessel 7 of FIG. 3 comprises a plurality of assemblies 1 wherein the assemblies are arranged side by side in a row for increasing the filtering area. Here, the assemblies 1 are arranged between the two floating bodies 15a, 15b. The vessel 7 comprises an adjusting device (not shown) which couples the assemblies 1 and the vessel 7 for adjusting the height position of the assemblies 1 relative to the water surface. Respective outlets 11 of at least two filtering devices 3 are coupled with a common conduit (not shown) for collecting residue. The vessel 7 comprises control means (not shown) such that the vessel 7 is an autonomous unmanned vessel 7. The vessel 7 is driven by driving means (not shown) using solar and/or wind power, preferably using only solar and/or wind power.

In use, the vessel 7 collects particles from sea in particular pollution, like plastic particles. The vessel drags the assembly at low travelling speed, like lower than 2 m/s, for example 1 m/s.

It will also be obvious that the above description and drawings are included to illustrate some embodiments of the invention, and not to limit the scope of protection. Starting from this disclosure, many more embodiments will be evident to a skilled person which are within the scope of protection and the essence of this invention and which are obvious combinations of prior art techniques and the disclosure of this patent.

The invention claimed is:

1. An assembly for being dragged by a vessel, the assembly comprising
   a filtering system comprising an inlet, and
   a fluidum guiding system
   defining a channel
   which increases in cross-sectional area from a fluidum inlet,
   wherein the inlet of the filtering system is at a position in or at the end of the channel at a point of largest cross-sectional area such that velocity of fluidum is reduced from the fluidum inlet to the inlet of the filtering system.

2. An assembly according to claim 1, wherein the fluidum guiding system at least partly encloses the filtering system.

3. An assembly according to claim 1, wherein the fluidum guiding system encloses substantially the entire filtering system.

4. An assembly according to claim 1, wherein the filtering system comprises a netting with a mesh configured such that particles of contamination are filtered out of the fluidum.

5. An assembly according to claim 1, wherein the filtering system comprises an outlet for allowing filtered out particles to leave the filtering system.

6. An assembly according to claim 1, wherein the fluidum guiding system comprises opposing side members and a bottom member which are joined together for defining the channel.

7. An assembly according to claim 6, wherein at least one side member comprises a curved portion (13).

8. Assembly according to claim 1, wherein the channel is open at its upper side.

9. A vessel comprising an assembly according to claim 1, wherein the assembly is connected to the vessel such that it can be dragged by the vessel.

10. A vessel according to claim 9, wherein the assembly couples to the vessel such that the height position of the assembly relative to the water surface can be adjusted.

11. A vessel according to claim 9, comprising a plurality of assemblies.

12. A vessel according to claim 11, wherein the plurality of assemblies are arranged side by side in a row.

13. A vessel according to claim 9, wherein each filtering system comprises an outlet and respective outlets of at least two filtering systems can be coupled.

14. A vessel according to claim 9, the vessel being driven using solar and/or wind power.

15. A vessel according to claim 9, wherein the vessel comprises control means such that the vessel is an autonomous unmanned vessel.

16. The assembly of claim 1, wherein the inlet of the filtering system is located at a midpoint of the channel, and the channel decreases in cross-sectional area after the location of the inlet of the filtering system.

17. The assembly of claim 1, wherein the sides of the fluidum guiding system defining the channel are curved.

18. A method for collecting particles from water bodies, the method comprising:
   providing at least one assembly comprising a fluidum guiding system defining a channel which expands in cross-sectional area from an inlet to an inlet of a filtering system;
   coupling said at least one assembly to a vessel; and
   placing the vessel in a water body to collect particles therefrom.

19. The method according to claim 18, wherein the vessel moves on the water body.

* * * * *